United States Patent [19]

Arnold

[11] Patent Number: 4,985,906

[45] Date of Patent: Jan. 15, 1991

[54] CALIBRATION PHANTOM FOR COMPUTER TOMOGRAPHY SYSTEM

[76] Inventor: Ben A. Arnold, 4 Sandstone, Irvine, Calif. 92714

[21] Appl. No.: 418,778

[22] Filed: Oct. 2, 1989

Related U.S. Application Data

[63] Continuation of Ser. No. 298,789, Jan. 18, 1989, abandoned, which is a continuation of Ser. No. 15,047, Feb. 17, 1987, abandoned.

[51] Int. Cl.$^5$ ............................................. G01N 23/00
[52] U.S. Cl. ...................................... 378/18; 378/207
[58] Field of Search ........................... 378/18, 20, 207; 250/363 SG

[56] References Cited

U.S. PATENT DOCUMENTS

| | | |
|---|---|---|
| 4,115,691 | 9/1978 | Oldendorf . |
| 4,124,799 | 11/1978 | Schittenhelm . |
| 4,233,507 | 11/1980 | Votz .................................... 378/207 |
| 4,649,561 | 3/1987 | Arnold ................................ 378/207 |
| 4,724,110 | 2/1988 | Arnold . |

FOREIGN PATENT DOCUMENTS 3006737 8/1983 Fed. Rep. of Germany .
402070 4/1974 U.S.S.R. .
425146 9/1974 U.S.S.R. .

OTHER PUBLICATIONS

Cann et al., "Spinal Mineral Loss in Oophorectomized Women," Jama, Nov. 7, 1980, vol. 244, No. 18.

*Primary Examiner*—Craig E. Church
*Attorney, Agent, or Firm*—Knobbe, Martens, Olson & Bear

[57] ABSTRACT

A calibration phantom for the quantitative computer tomography (QCT) system for bone or other tissue measurement in which a series of graduated reference solutions are retained within cavities formed in a translucent member having x-ray attenuation characteristics closely approximate to human tissue. In preferred embodiment, the reference solutions are sealed under pressure in direct contact with the material forming the base of the phantom. Only a very thin wall separates the solution from the upper and lower surfaces of the phantom. In addition, the cavities are closely adjacent one another. As a result, phantoms constructed in accordance with this invention minimize the size and mass of the phantom and thus minimize x-ray beam hardening, scatter and image are the facts.

4 Claims, 2 Drawing Sheets

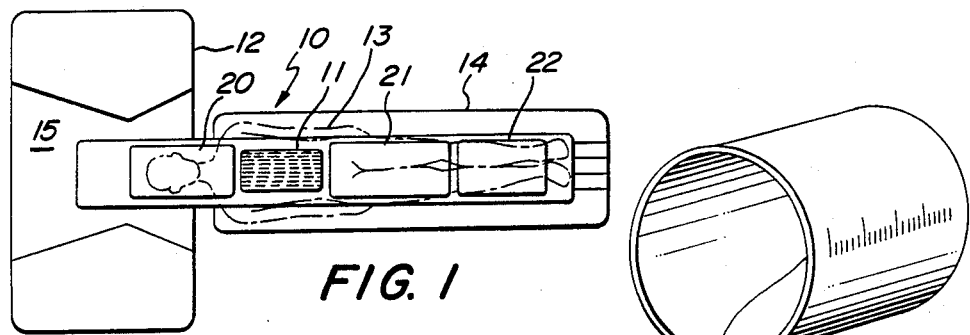
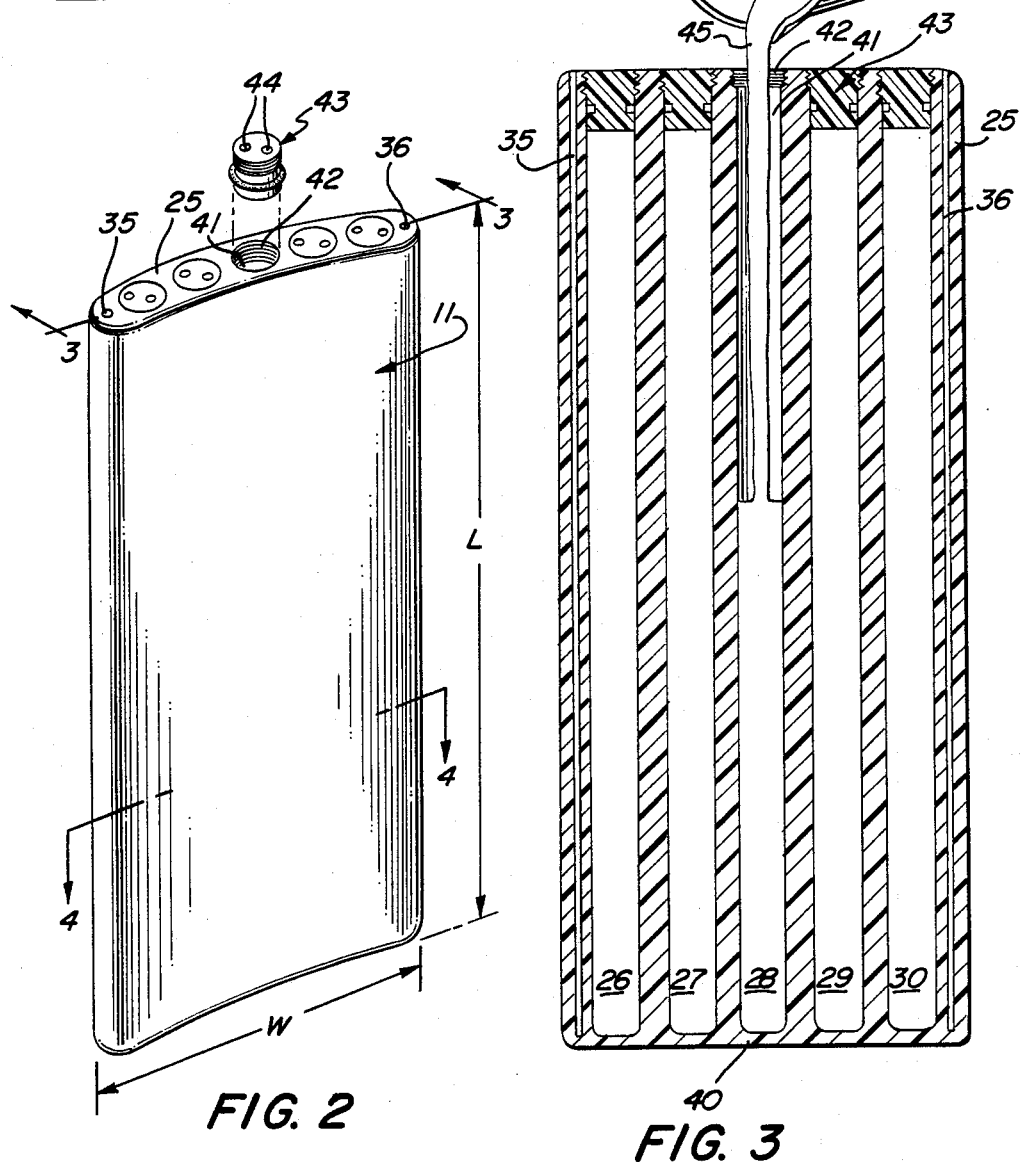

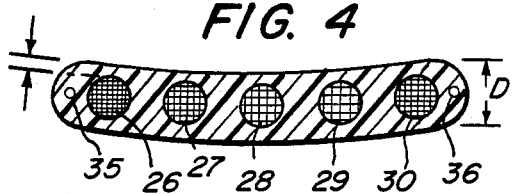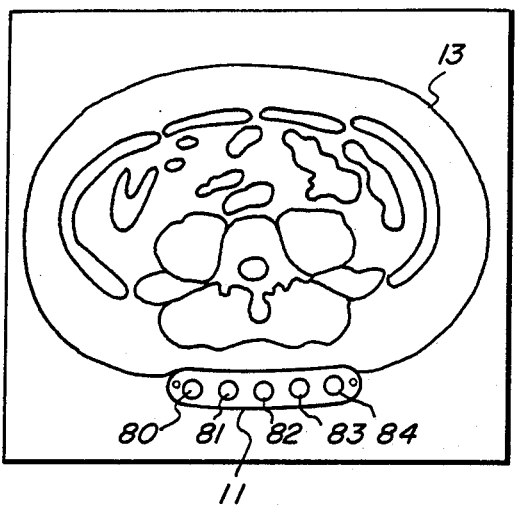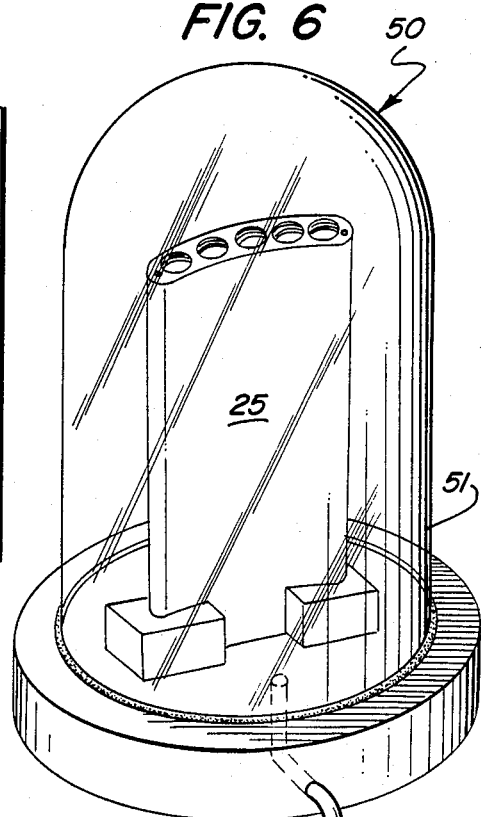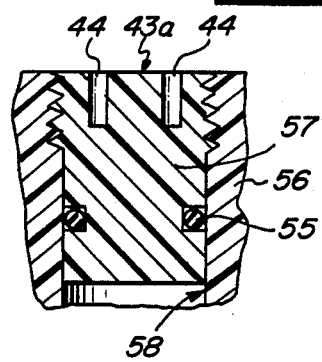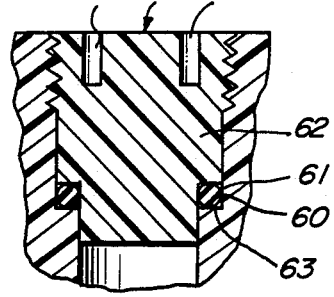

CALIBRATION PHANTOM FOR COMPUTER TOMOGRAPHY SYSTEM

This is a continuation of Ser. No. 07/298,789 filed Jan. 18, 1989 now abandoned which is a continuation of Ser. No. 07/015,047 filed Feb. 17, 1987 now abandoned.

BACKGROUND OF THE INVENTION

The use of calibration reference phantoms for use with computerized tomography (CT) systems has been clinically demonstrated at the University of California, San Francisco, to provide substantial enhancement in the utilization of such systems for bone density measurements. Such quantitative computer tomography (QCT) systems have in more than 300 clinical installations, provided early detection and precise long-term monitoring of osteoporosis patients. The original patent for the calibration phantom is (U.S. Pat. No. 4,233,507—Donald J. Volz) disclosed the general technique of using a calibration phantom scanned simultaneously with the patient. As described in this patent, the phantom is located underneath the patient and it and the patient are scanned simultaneously with the CT scanner thus providing a standard reference for correction of various technical factors in the CT process for improved performance. The phantom provides a series of reference elements whose graduated densities correspond to varying human bone mineral contents such that the operator can manually (or more recently with a preprogrammed computer) calculate the bone mineral density of the patient.

SUMMARY OF THE INVENTION

The present invention relates to an improved calibration phantom as taught by Dr. Donald J. Volz in U.S. Pat. No. 4,233,507.

In the preferred embodiment as described hereinafter, the phantom comprises a molded base member formed of urethane having a series of closely spaced, elongated, cylindrical cavities formed within the urethane base member. A plurality of these cavities are filled with predetermined concentrations of a solution having x-ray attenuation coefficient corresponding to human bone and one cavity is filled with distilled water. These solutions directly contact the urethane material, i.e., the solutions are in direct contact with the base material of the phantom which thus forms the container as well as the support material. Prior to sealing, the filled cavities are subject to a degassing procedure to ensure that substantially all gas and gas bubbles are removed from the solutions. Each cavity is then capped with a closure advantageously designed as a vacuum tight seal and to exert a substantial pressure on the encapsulated solutions and maintain such pressure over the life of the phantom.

The construction of the phantom in this manner provides a high strength phantom with low permeability to liquids and gasses. The lower physical density and Atomic Number of the urethane material product reduces total x-ray attenuation for reduced beam hardening and x-ray scatter over prior art phantoms.

The resulting phantoms constructed in accordance with this invention have a number of significant advantages.

1. The phantoms have x-ray attenuation properties closely approximate to human muscle. Human muscle tissue typically has a CT number of approximately 32 expressed in "H-units" and phantoms constructed in accordance with this invention have CT numbers generally in the range of about 12 to 33 H-units. As a result, x-ray interactions in the phantom are closely approximate to human muscle and bone. Image artifacts in the phantom images are reduced due to the similarity of x-ray attenuation and scatter in the phantom and patient which are in close proximity to each other.

2. Urethane is a very strong and unbreakable material thus overcoming the fragile properties of prior art phantoms. In addition, the wall thickness of the cavities can be significantly reduced such that the phantom, as a whole, can be considerably narrower and thinner than the prior art phantoms. This reduced size and total mass provides for less beam hardening and scatter and also for improved ease of positioning of the patient on the table and in the CT scanner field of view. Also, the radiation dose to the patient is reduced due to the overall reduced attenuation. The high strength of the urethane further facilitates the use of high pressure on the reference solutions.

3. The urethane material has an extremely low permeability to water and gases. As a result, the integrity of the reference solutions is maintained over a long time period. In addition, the low permeability of the urethane material permits the wall thickness to be made extremely thin between the upper and lower surfaces of the phantom and the reference cavities. The reduced wall thickness and therefore reduced phantom size further produces less beam hardening and scatter and therefore reduced image artifacts.

4. The chemistry of the urethane material can be selected to provide a rigid phantom or, if desired, a flexible phantom which an be contoured to various shapes including contouring to the patient's body.

5. The urethane material is translucent which permits visual verification of the absence of gas bubbles in the reference elements.

6. The liquid reference elements and urethane base provide for very homogeneous x-ray attenuation properties which provides minimal structure variations in attenuation i.e., structure noise in the CT image. This increases the precision of the quantitative measurements.

The conventional teaching of the prior art is that the solution containers are of a different material than the phantom base material. Typically, sealed thin wall polyethylene tubes filled with the reference solutions are embedded in an acrylic base. The x-ray attenuation properties of these prior art phantoms—their base materials, typically having a CT number of approximately 80H-units—are considerably higher than human muscle tissue.

Moreover, the prior art phantoms require that the base member be a physically large and heavy member in which there is a substantial thickness of material (a) between the tube of reference solution and the outer wall of the phantom, and (b) between adjacent tubes. This substantial size and mass of base material produces significant x-ray scattering and beam hardening of the x-ray beams and increased image artifacts.

The present invention is therefore a substantial departure from and quite distinctive over the prior art phantom since the phantom base itself provides the reference solution containers while having a number of significant advantages over the prior art devices.

BRIEF DESCRIPTION OF THE DRAWINGS

FIG. 1 is an elevation view of a computer tomography system showing the calibration phantom in position;

FIG. 2 is an exploded perspective view showing the placement of a cavity plug on the phantom base;

FIG. 3 is a sectional view along the line 3—3 of FIG. 2 showing the filling of the calibration phantom with a reference solution;

FIG. 4 is sectional view taken along the line 4—4 showing reference cavities having a circular cross-sectional configuration;

FIG. 5 is a sectional view of another embodiment of the calibration phantom showing reference cavities having a generally square cross-sectional configuration;

FIG. 6 is a perspective view showing the use of a vacuum pump and bell jar for degassing the reference solutions during the manufacture of the calibration phantom;

FIG. 7 is a diagramatic representation of a typical transaxial tomographic slice provided by the CT scan.

FIG. 8 is a cross-sectional view of one embodiment of the plug used to seal the reference cavities of the phantom base; and FIG. 9 is a cross-sectional view of a second embodiment of a sealing plug used to seal the reference cavities of the phantom base.

DETAILED DESCRIPTION OF THE INVENTION

Referring now to FIG. 1, an overhead view of a conventional CT scanner 10 is shown illustrating the position of a calibration phantom 11. As shown, the CT scanner includes a gantry 12. Although not shown, it will be understood that, as is well known, the gantry 12 supports an x-ray source and collimator and a juxtaposed x-ray detector. The patient 13 is positioned on a movable table 14 which is translated through the gantry opening 15. As shown, a series of cushions 20, 21 and 22 are supported by the table, as well as the calibration phantom 11. A bolus bag containing a water equivalent gel (not shown) may in some cases be placed between the top of the phantom and the patent to eliminate or reduce the air gap between the phantom and the curve of the patient's body.

As in the Volz patent, supra, phantoms of this invention comprise a series of elongated samples of reference materials extending longitudinally with the table top and translatable with the table and patient such that each slice of the CT scan includes both the patient and the calibration phantom for that portion of the body overlying the phantom.

The configuration and physical construction of the calibration phantom is shown in FIGS. 2-6, 8 and 9. As shown, the phantom 11 comprises an elongated, slightly arcuate base 25 advantageously molded as a single member with a plurality of elongated cavities 26, 27, 28, 29 and 30 spaced side-by-side therein. In addition, elongated small diameter metallic rods 35 and 36 may be molded into the base 25 and manually used by the operator or automatically by the CT scanner system to locate the CT cursor to a region of interest in the image.

Each of the cavities 26–30 is advantageously molded with a closed end 40 and an open end 41. In the preferred embodiment of the invention, the open end 41 is threaded as shown at 42 to receive a screw cap and O-ring sealing member 43. A pair of apertures 44 (best shown in FIGS. 8 and 9) are provided to receive a plug tool to rotate the plug within threaded opening 41 to the desired depth.

The preferred material for constructing the base 25 and sealing plugs 43 is a urethane formed by combining in a reaction injection mold (RIM) an aliphatic isocyanate and polyether resin as well as one or more catalyst and stabilizer additives. The particular formulation member of the urethane used to construct the present phantoms is formulation No. GMC-462 supplied by Good Marc Chemicals, Inc., Costa Mesa, Calif. The stabilizers and or catalysts are utilized to prevent discoloration or yellowing of the urethane upon extended radiant exposure as well as to control solidification rates and temperature and hardness. The particular aliphatic urethane utilized in the present invention has the properties of being stable in the presence of water without the loss or breakdown of material, low viscosity to allow molding without the production of air bubbles in the phantom base, and a physical density of approximately 1.03 to 1.07 grams per cubic centimeter. The urethane is of a water white color which is UV stabilized thereby avoiding yellowing and may additionally be advantageously dyed to provide a distinctive color.

The resultant phantom base 25 is an extremely strong container for the reference calibration elements while also having a very low permeability to water and gases. As a result, the wall thickness between the upper and lower surfaces of the phantom base and the juxtaposed cavity wall (the wall thickness T as shown in FIG. 4) can be very thin, typically 3 mm in thickness. As a result, in a phantom of a given size, the tubular cavities 26–30 have as large a cross section as is possible in a phantom of a given size so as to enhance photon statistics for improved precision while minimizing beam hardening and x-ray scatter and reducing image artifacts. In addition, the nonpermeable, high strength walls allow liquid calibration samples to be maintained under high pressure so as to ensure a stable reference over a long period of time by inhibiting any ingress or egress of water or gas or the formation of air bubbles. It is important to note that the reference solutions are used for medical diagnosis, so there x-ray attenuation properties must be known and maintained to a high accuracy for long time periods.

The urethane material is also particularly advantageous in providing a homogeneous phantom without attenuation variations across the cross section of the phantom body. Moreover, the urethane material is translucent so that any gas bubbles in the liquid reference solutions can be readily observed visually. Further, as described below, the physical characteristics of the urethane material can be varied to provide either rigid phantoms or flexible phantoms that can be contoured to the patient's body.

As described in the Volz patent, supra, several of the calibration samples are advantageously formed of a series of graduated various concentrations of dipotassium hydrogen phosphate solutions ($K_2HPO_4$) having x-ray attenuation coefficients corresponding to human bone. Calcium carbonate ($CaCO_3$) and calcium hydroxyapatite $Ca_5(PO_4)_3(OH)$ may be also used to simulate human bone x-ray attenuation. It will, of course, be understood that the present invention is not limited only to bone mineral analysis systems but may contain samples having different tissue-like attenuation properties such as human muscle and blood with iodine contrast materials which may be substituted in the phantoms for calibrating the CT scanner for other diagnostic uses.

The steps of manufacturing the calibration phantom 11 are shown in FIGS. 3 and 6. As shown in FIG. 3, the base cavity 28 is being filled with the calibrated reference solution 45. As shown in FIG. 6, after each of the cavities 26–30 has been filled with its own calibrated solution, the entire base member 25 is placed in a suitable degassing chamber 50. Chamber 50 comprises a conventional vacuum system including a bell jar 51 and vacuum pump or other source 52 for evacuating the chamber within the bell jar 51 to extract the gas and bubbles out of the respective solutions. It has been found to be advantageous to loosely retain the sealing member 43 on each of the cavities filled with solution so as to prevent loss of the liquid vapor or change of concentrations of the solution samples, thus avoiding any change in their x-ray attenuation coefficients which must be maintained to a high accuracy.

Another technique for degassing the solutions is to lower the filled base 25 into a water bath coupled to an ultrasonic transducer (not shown) and eliminate any gas bubbles in the reference solutions by ultrasonic cavitation. A standard ultrasonic bath cleaner of 4D KHz frequency may be used. As a result, whichever degassing technique is employed, any gas which is in the calibrated solutions or which enters when the solution is poured into the cavity or any gas bubbles which are trapped on the walls of the cavity will be removed prior to the final sealing of the reference solutions.

Alternate embodiments of the sealing member 43 are shown in FIGS. 8 and 9. In the embodiment 43a of FIG. 8, an O-ring 55 is retained in an annular groove 56 in the side wall of the screw plug 57 so as to provide a tight O-ring seal between the plug 57 and the side wall 58 of the cavity. In another embodiment 43b, the O-ring 60 is retained at the bottom of the shoulder 61 found on the plug 62 so that the seal is formed as the plug 62 forces the O-ring against an abutment 63 in the cavity opening. The sealing members 43a and 43b are screwed into the threaded cavity openings of the phantom base sufficiently far so as to exert a substantial pressure, i.e., on the order of 100 psi, on the encapsulated liquid calibrated reference solutions. Air bubble formation is therefore further prevented.

In the embodiment shown in FIG. 4, the cavities 26–30 are formed with a circular cross-sectional configuration. In an alternative embodiment, the cavities 70, 71, 72, 73, and 74 are formed with a generally square configuration which makes a somewhat more efficient utilization of the interior space of the base member. Both embodiments, however, may be made quite compact while maintaining calibration cavity diameters of requisite diameter, e.g., 2.0 cm. Thus, in one embodiment of the calibration phantom having the external configuration of FIG. 2 and the cross-sectional configuration of FIGS. 3 and 7, the overall configuration of the base member is slightly crescent shaped with a radius of curvature on the concave side of 55.8 cm., a length L of 36 cm., a width W of 16 cm., and a depth D of 2.6 cm., and each of the cavities 21–36 are each 2.0 cm in diameter. The total weight is 3.5 lbs.

In contrast, the acrylic based prior art phantoms presently in use are significantly larger and heavier having typically a length of 46 cm., a width of 26.5 cm., and a depth of 4 cm resulting in a total weight of 10.5 lbs. Since the tubes embedded in these prior art phantoms are approximately the same diameter as the cavities of the present invention, it will be apparent that in the prior art, a substantially greater thickness of base material is present between the upper and lower surfaces of the phantom and the walls of the reference samples and between the reference elements than in the phantoms constructed in accordance with this invention.

A depicted typical CT cross-sectional image showing a properly positioned patient 13 and phantom 11 is shown in FIG. 7. Typically, four of the phantom's reference elements 80, 81, 82 and 83 provide a calibration for calculating the bone mineral density in the vertebrae of the patient, (the concentrations of $K_2HPO_4$ in distilled water are typically 0, 50, 100 and 200 mg/cc. and the fifth (element 84, for example) is a fat equivalent reference sample. In a typical examination, the mineral content for four vertebral bodies is obtained and averaged to obtain a single result for the patient.

The hardness and rigidity of the phantom may be modified by changes in chemistry of the urethanes. Thus, a rigid phantom may be constructed using the urethane material whereas the urethane chemistry may be changed using conventional techniques to provide for a flexible phantom base which can be contoured to various shapes including contouring to the patient's body. For example, the flexible phantom could be contoured to the spine, hip, or leg of the patient.

It will also be understood that the calibration samples need not be of a liquid composition. Thus, the samples can be constructed of a mixture of urethane with $K_2HPO_4$ or urethane with calcium hydroxyapatite to construct solid rods which are then located in the hollow cavities in place of the liquid solutions. Alternatively, the solid material calibration samples can be attached directly to each other to form the solid phantom such that all or substantially all of the phantom is comprised of the solid sample elements.

It will also be understood that the calibration samples and the phantom base member can be formed from other plastic like materials having the desired physical and x-ray attenuation properties, for example a polyolefin polymer sold under the trademark TPX by Mitsui Petrochemical Industries, Ltd. can be used and for the added advantage of being injection molded.

I claim:

1. A calibration phantom for a quantitative computerized tomography (QCT) system of bone mineral measurement in which a series of graduated reference samples having x-ray attenuation characteristics closely proximate to human tissue are retained within cavities integral with the material forming the phantom base and wherein said cavities are located closely proximate the upper and lower surfaces of said phantom so as to reduce the size and mass of the phantom and thus reduce x-ray base hardening, scatter and image artifacts, comprising:

a base formed of a material having x-ray attenuation properties with a CT number closely approximate to human tissue;

a plurality of elongated cavities formed in said base, so that the upper and lower surfaces of said base are closely proximate said cavities with a thickness of less than one cm of base material between the upper surface and lower surface of said base and said cavities;

a series of graduated concentrations of reference samples having x-ray attenuation characteristics corresponding to human bone retained within said cavities such that the samples are indirect contact with the base material; and a closure which seals the cavity to encapsulate the samples within said cavity.

2. The calibration phantom of claim 1 wherein said base is formed of a urethane material.

3. The calibration phantom of claim 1 in which said cavity has an open end which is threaded to mate with corresponding threads on said closure, said closure having a shoulder formed thereon and said cavity having a juxtaposed abutment with an O-ring located therebetween such that as the closure is screwed into the cavity opening, pressure is simultaneously exerted on the reference samples while also being exerted on the O-ring so as to maintain said reference samples under positive pressure and provide a tight seal against ingress and egress of liquids and gases to and from reference samples retained within said cavity.

4. A calibration reference phantom for use in a CT system in which the x-ray beam of the CT scanner passes through a patient and the phantom simultaneously in which the calibration reference samples are located in direct contact with a material having x-ray attenuation characteristics corresponding to human tissue so as to minimize image artifacts, comprising:

a component formed of a material having x-ray attenuation properties closely approximate to human tissue;

a plurality of elongated samples surrounded by said component; and a series of reference samples retained within said component such that the samples are in direct contact with the tissue equivalent component, said reference samples having x-ray attenuation characteristics corresponding to human bone or tissue so that the x-ray beam of the CT scanner passes through only material having x-ray attenuation characteristics corresponding to human tissue or through the reference samples, so as to reduce image artifacts.

* * * * *